United States Patent
Maerz et al.

(10) Patent No.: US 6,663,889 B1
(45) Date of Patent: Dec. 16, 2003

(54) AMBROXOL-CONTAINING LOZENGE

(75) Inventors: Frieder Ulrich Maerz, Soergenloch (DE); Holger Hans-Hermann Von Der Heydt, Alzey (DE); Horst Schmitt, Nieder-Hilbersheim (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 49 days.

(21) Appl. No.: 10/031,580

(22) PCT Filed: Jul. 7, 2000

(86) PCT No.: PCT/EP00/06437

§ 371 (c)(1), (2), (4) Date: Apr. 23, 2002

(87) PCT Pub. No.: WO01/05378

PCT Pub. Date: Jan. 25, 2001

(30) Foreign Application Priority Data

Jul. 20, 1999 (DE) .......................... 199 33 148

(51) Int. Cl.⁷ .................... A61K 9/20; A61K 31/135
(52) U.S. Cl. .................... 424/464; 424/465; 424/468; 424/469
(58) Field of Search .................... 424/464, 465, 424/468, 469

(56) References Cited

U.S. PATENT DOCUMENTS 6,066,335 A * 5/2000 Machoczek ................. 424/466

FOREIGN PATENT DOCUMENTS

| DE | 3034975 A1 | 4/1982 |
| EP | 0 138 020 A2 | 4/1985 |
| EP | 0 546 846 A1 | 6/1993 |
| EP | 0 687 464 A2 | 12/1995 |

OTHER PUBLICATIONS

Gruber, et al; "Presskammerbeschichtung, ein Beitrag zur Optimierung der Tablettenherstellung"; Pharmazeutische Industrie, vol. 50, 1988, 839–845.

* cited by examiner

*Primary Examiner*—Thruman K. Page
*Assistant Examiner*—Rachel M. Bennett
(74) *Attorney, Agent, or Firm*—Robert P. Raymond; Philip I. Datlow; Alan R. Stempel

(57) ABSTRACT

The present invention relates to a new tablet for sucking containing the active substance ambroxol and having improved properties.

19 Claims, No Drawings

AMBROXOL-CONTAINING LOZENGE

This application is a 371 of PCT/EP00/06437 filed Jul. 7, 2000.

The present invention relates to a new tablet for sucking containing the active substance ambroxol and having improved properties.

Trans-4-(2-Amino-3,5-dibromobenzylamino)-cyclohexanol which is known by the international generic name ambroxol has been successfully used for decades in the form of its hydrochloride as a secretion-releasing expectorant [Hagers Handbuch der Pharmazeutischen Praxis (edited by List and Hörhammer), 4$^{th}$ edition, 1967–1989, Bruchhausen et al., 5$^{th}$ edition, 9$^{th}$ volume, Springer, Berlin 1993–1995), (5.) 7, 155–159; Pharm. Ztg, 138, (1993) 2754].

The aim of the present invention is to make ambroxol into a pharmaceutical form which acts locally in the pharyngeal cavity in the form of a tablet for sucking. For a suckable tablet of this kind to gain acceptance by the patient, apart from the efficacy the sensory impression is crucial. Another important point is the safety of the drug, i.e. steps must be taken to ensure that the intended quantity of active substance can be administered to the patient without any undesirable by-products or breakdown products which may arise after lengthy storage of the preparation.

Breakdown products of this kind may be formed for various reasons, e.g. as a result of the thermal instability of the active substances or as a result of interactions, e.g. breakdown reactions which the active substance enters into with the pharmaceutical excipients or the packaging materials or which are catalysed by these materials.

Hitherto, apart from an interaction with formaldehyde or formaldehyde-cleaving compounds, there have been no reports of incompatibilities in connection with the active substance ambroxol, which has been known in pharmaceutical science for many years. Apart from the safety and efficacy of the drug, good flavour, sufficient sweetness and a pleasant texture or a pleasant mouth feel, among other things, play an important part in the acceptance of a suckable tablet by the patient, as already mentioned above. These conditions can be met by a suitable choice of excipients such as flavourings or sweeteners.

It should also be borne in mind that the formulation of a suckable tablet with a drug intended for local application requires inter alia a matrix-forming agent which dissolves evenly in the mouth and thereby releases the active substance. Since the drug interacts with the taste buds for a fairly long time, the sensory impression should be acceptable to the patient. In the prior art, so-called sugar alcohols are used as the matrix materials.

By sugar alcohols are meant a group of monosaccharides which are obtained by reducing the carbonyl function. Polyhydroxy compounds of this kind which are not sugars but still taste sweet are commonly used as sugar substitutes. These generally crystalline water-soluble polyols are differentiated according to the number of hydroxy groups contained in the molecule, into tetritols, pentitols, hexitols etc. Examples of naturally occurring sugar alcohols are glycerol, threitol and erythritol, adonitol (ribitol), arabitol (formerly lyxitol) and xylitol, dulcitol (galactitol), mannitol and sorbitol (glucitol or sorbitol) [Cf. Römpp, Lexikon Chemie, Georg Thieme Verlag Stuttgart/New York 1998; Belitz-Grosch (3.), p. 701; Karrer, No. 139–158, 5401–5410; Kirk-Othmer 1, 569–588; (3.) 1, 754–777].

In addition, systems of this kind should expediently contain excipients which make these tablets industrially easier to handle. For example, it is undesirable for the tablets to have any sticky qualities which might lead to a risk of the tablets sticking together or sticking to the tool surfaces and interfering with the industrial manufacturing process. Moreover, from the patient's point of view it is undesirable for the tablet to be difficult to remove from the packaging, on account of its stickiness, for example. Consequently, in practice, so-called release agents or lubricants are added to tablets of this kind. So-called metal soaps such as calcium or magnesium stearate or calcium arachinate are conventionally used [U. I. Leinonen, H. U. Jalonen, P. A. Vihervaara, E. S. U. Laine: Physical and Lubrication Properties of Magnesium Stearate, Journal of Pharmaceutical Sciences 81 (1992) 1194–1197].

Surprisingly, it has now been found that when preparing ambroxol hydrochloride in one of the usual flavoured bases prepared from sugar alcohols—particularly when using sorbitol as the matrix material—and using magnesium stearate as mould release agent, the stability tests detected a by-product of as yet unexplained chemical structure which had not hitherto been found and the occurrence of which depends greatly on the particular storage temperature.

As the presence of a by-product or breakdown product in a drug is never acceptable the problem thus arises of finding a preparation in the form of a suckable tablet which fully conforms to the drug safety requirements in this respect in particular.

First of all, one possible alternative is to replace the matrix material.

However, using sucrose, which is also known from the prior art as a matrix material, tablets of sufficient hardness can only be produced by using high compressive forces. Furthermore, this excipient causes caries.

The use of sorbitol, on the other hand, yields tablets of sufficient hardness and does not cause caries. On the other hand, this sugar alcohol has a serious tendency to adhere to the tablet-making tools, making the addition of a release agent absolutely essential.

Surprisingly, it has now been found that a tablet for sucking containing ambroxol based on sugar alcohols, particularly sorbitol, as matrix material can be obtained using a polyethyleneglycol and a pharmaceutically acceptable laminar silicate—particularly talc—as lubricant or release agent, in which the formation of a by-product cannot be detected, or is below the detection limits, even after lengthy storage.

The polyethyleneglycols which may be used according to the invention expediently have a molecular weight in the range from 3,500 to 20,000. A polyethyleneglycol with a molecular weight in the range from 4,000 to 12,000 is preferred, while a polyethyleneglycol with a molecular weight of about 6,000 is particularly preferred. A polyethyleneglycol of this kind is known from the prior art under the name Macrogol 6000.

The talc which is preferably used is generally a—common—hydrated magnesium silicate of the composition $Mg_3[(OH)_2/Si_4O_{10}]$ or $3\ MgO_4.SiO_2$. However, it is also possible to use another phyllosilicate which is acceptable from a pharmaceutical point of view.

The amount of talc in a tablet for sucking according to the invention with a total mass of 1.5 g is in the range from 5 to 100 mg, preferably 20 to 80 mg, more preferably 30 to 60 mg and most preferably 60 mg.

The amount of active substance—in this case ambroxol—depends on the desired dosage and is also variable within a wide range. Conveniently, the proportion of active substance in a tablet for sucking is in the range from 1 to 50 mg, preferably 5 to 30 mg and most preferably in the range from 10 to 25 mg of ambroxol in the form of its hydrochloride.

The quantities of the other excipients or flavourings are not critical and may be adapted within wide limits to suit the particular requirements.

The Examples which follow illustrate the present invention without restricting it thereto:
Examples of formulations:

| Composition A: | |
|---|---|
| ambroxol HCl: | 10.0 mg |
| peppermint flavour: | 16.0 mg |
| saccharine - Na: | 0.5 mg |
| sorbitol: | 1458.5 mg |
| magnesium stearate: | 15.0 mg |
| total mass: | 1500.0 mg |

Composition A is a comparative composition.

Compositions A and C are prepared by conventional direct compressing technology.

| Composition B: | |
|---|---|
| ambroxol HCl: | 10.0 mg |
| peppermint flavour: | 16.0 mg |
| saccharine - Na: | 0.5 mg |
| sorbitol: | 1438.5 mg |
| Macrogol 6000: | 30.0 mg |
| talc: | 5.0 mg |
| total mass: | 1500.0 mg |

Composition B was produced by applying the talc only to the tablet surface using the compression chamber coating method [Gruber, Gläsel, Liske: Preßkammerbeschichtung, ein Beitrag zur Optimierung der Tablettenherstellung, Pharm Ind. 50 (1988) 839–845].

| Composition C: | |
|---|---|
| ambroxol HCl: | 20.0 mg |
| peppermint flavour | 16.0 mg |
| saccharine - Na: | 0.5 mg |
| sorbitol: | 1403.5 mg |
| Macrogol 6000 | 30.0 mg |
| talc | 30.0 mg |
| total mass: | 1500.0 mg |

The Table which follows shows the various contents of decomposition product in the individual preparations:

Formation of breakdown product in the Examples in %*

| Packaging: Storage conditions | Polypropylene tubes | | | | | |
|---|---|---|---|---|---|---|
| length of storage | 25° C./60% rel.hum. | | | 30° C./70% rel.hum. | | |
| (mths.) | A | B | C | A | B | C |
| 0 | <0.2 | <0.2 | <0.2 | <0.2 | <0.2 | <0.2 |
| 3 | <0.2 | <0.2 | n.d. | 0.27 | <0.2 | <0.2 |
| 6 | <0.2 | <0.2 | n.d. | 0.34 | <0.2 | <0.2 |
| 12 | 0.26 | <0.2 | n.d. | 0.89 | <0.2 | <0.2 |
| 24 | 0.53 | <0.2 | n.d. | 1.80 | 0.32 | <0.2 |

*breakdown product in peak areas-% based on the content of active substance; rel.hum. = relative humidity As can clearly be seen from the Table, under most conditions the proportion of breakdown product in each formulation according to the present invention is less than 0.2% or below the limits of detection.

What is claimed is:

1. A tablet for sucking comprising ambroxol, a sugar alcohol as a matrix material, a pharmaceutically acceptable laminar silicate and a polyethyleneglycol, optionally together with one or more other pharmaceutical excipients, taste enhancers or flavourings.

2. A tablet for sucking according to claim 1, characterised in that the laminar silicate is talc.

3. A tablet for sucking according to claim 1 or 2, characterised in that the content of laminar silicate is in the range from 5 to 100 mg, based on a total mass of the tablet of 1.5 g.

4. A tablet for sucking according to claim 3, characterised in that the content of laminar silicate is in the range from 20 to 80 mg, based on a total mass of the tablet of 1.5 g.

5. A tablet for sucking according to claim 4, characterised in that the content of laminar silicate is in the range from 30 to 60 mg, based on a total mass of the tablet of 1.5 g.

6. A tablet for sucking according to claim 5, characterised in that the content of laminar silicate is 60 mg, based on a total mass of the tablet of 1.5 g.

7. A tablet for sucking according to claim 1 or 2, characterised in that the ambroxol is in the form of its hydrochloride and is present in the range from 1 to 50 mg, based on a total mass of the tablet of 1.5 g.

8. A tablet for sucking according to claim 7, characterised in that the content of ambroxol hydrochloride is in the range from 5 to 30 mg, based on a total mass of the tablet of 1.5 g.

9. A tablet for sucking according to claim 8, characterised in that the content of ambroxol hydrochloride is in the range from 10 to 25 mg, based on a total mass of the tablet of 1.5 g.

10. A tablet for sucking according to claim 1 or 2, characterised in that the polyethyleneglycol has a molecular weight in the range from 3,500 to 20,000.

11. A tablet for sucking according to claim 10, characterised in that the polyethyleneglycol has a molecular weight in the range from 4,000 to 12,000.

12. A tablet for sucking according to claim 11, characterised in that the polyethyleneglycol has a molecular weight of 6,000.

13. A tablet for sucking according to claim 1 or 2, characterised in that the sugar alcohol is sorbitol.

14. A tablet for sucking according to claim 1 or 2, comprising a sodium salt of saccharine as a sweetener.

15. A tablet for sucking according to claim 1 or 2, comprising peppermint flavouring.

16. A process for preparing a tablet for sucking according to claim 1, characterised in that the individual components are mixed together and compressed to form a tablet.

17. A process according to claim 16, characterised in that the tablet is prepared by direct compression.

18. A process according to claim 16, characterised in that the laminar silicate is applied by the compression chamber coating method.

19. A method of administering ambroxol to a patient comprising administering to the patient a tablet for sucking according to claim 1.

* * * * *